United States Patent [19]

Persson et al.

[11] Patent Number: 5,520,931
[45] Date of Patent: May 28, 1996

[54] CONTROLLED RELEASE MORPHINE PREPARATION

[75] Inventors: Christiane Persson, Bjärred; Staffan Waxegård, Malmö; Sören Kulstad, Rydebäck; Lennart Frigren, Höllviken, all of Sweden

[73] Assignee: Gacell Laboratories AB, Malmö, Sweden

[21] Appl. No.: 362,526

[22] Filed: Jan. 4, 1995

Related U.S. Application Date

[62] Division of PCT/SE93/00642 published as WO94/03161, Feb. 17, 1994.

[30] Foreign Application Priority Data

Jul. 29, 1992 [SE] Sweden ................... 9202250

[51] Int. Cl.[6] ........................ A61K 9/22
[52] U.S. Cl. ............. 424/473; 424/464; 424/468
[58] Field of Search ................... 424/473, 464, 424/468

[56] References Cited

U.S. PATENT DOCUMENTS

| 4,461,598 | 7/1984 | Flechs ................................ 405/181 |
| 4,557,925 | 12/1985 | Lindahl et al. .................. 424/482 |
| 4,970,075 | 11/1990 | Oshlack ............................. 424/451 |
| 4,996,047 | 2/1991 | Kelleher et al. ................ 424/486 |
| 5,178,868 | 1/1993 | Malmqvist-Grandlund et al. .. 424/490 |

FOREIGN PATENT DOCUMENTS

| 0097523 | 1/1984 | European Pat. Off. . |
| 0205282 | 12/1986 | European Pat. Off. . |
| 0367746 | 5/1990 | European Pat. Off. . |
| 0365947 | 5/1990 | European Pat. Off. . |
| 0377518 | 11/1990 | European Pat. Off. . |
| 295548 | 11/1991 | Germany . |

OTHER PUBLICATIONS

"The United States Experience with Oral Controlled-Release Morphine (MS Contin Tablets)", Cancer 63:2348–2354, Jun. 1 Supplement 1989, Robert F. Kaiko et al.

*Primary Examiner*—D. Gabrielle Phelan
*Attorney, Agent, or Firm*—Burns, Doane, Swecker & Mathis

[57] ABSTRACT

The present invention concerns an oral morphine preparation having essentially complete bioavailability and, for the major part of the dissolution, an essentially zero order and essentially pH independent release of morphine for a period of at least 8 hours, preferably at least 12 hours, during which a period less than 100% is dissolved. In the preparation, the morphine, in the form of an easily soluble salt, is present in a combination with a buffering agent in a preparation coated with a diffusion membrane.

27 Claims, 1 Drawing Sheet

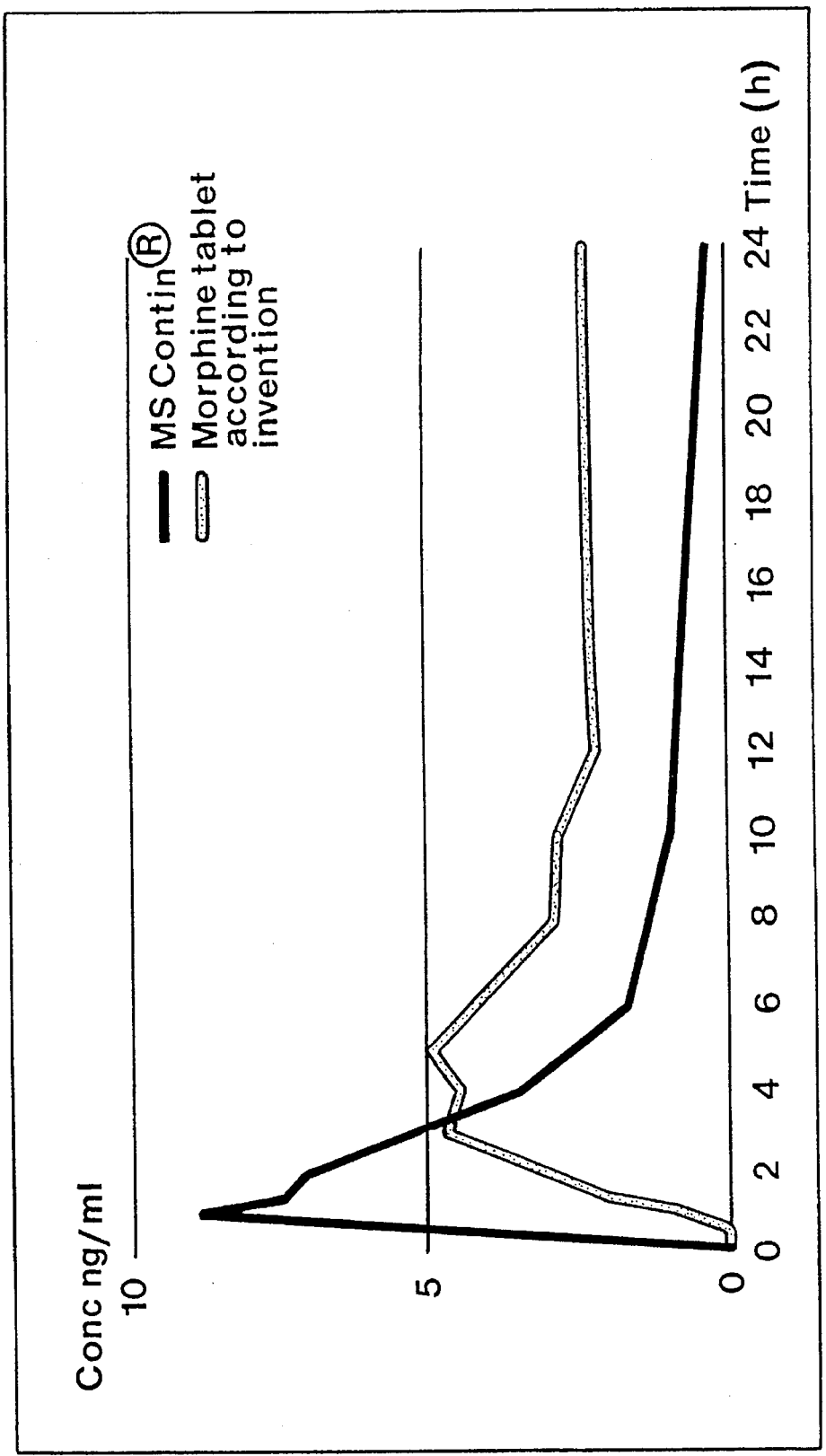

CONTROLLED RELEASE MORPHINE PREPARATION

This application is a 371 of PCT/SE93/00642, filed Jul. 28, 1993, published as WO94/03161, Feb. 17, 1994.

The present invention concerns a controlled release morphine preparation. Specifically the invention concerns a controlled release morphine oral preparation for once daily administration especially in cancer pain therapy.

BACKGROUND OF THE INVENTION

Cancer is a major world problem. Every year nearly 6 million new patients are diagnosed and more than 5 millions die. For patients suffering of cancer pain is a common problem and an analysis of 32 published reviews revealed that 70% of patients with advanced cancer had pain as a major symptom. From available data it is not possible to give a precise figure for the world-wide prevalence of cancer pain because the total number of cancer patients receiving treatment is not known. A conservative estimate is that every day at least 3.5 million people are suffering from cancer pain. This pain is an important but neglected public health issue in developed and developing countries. Effective pain management particularly in patients with advanced disease is one of four priorities in a comprehensive WHO cancer programme. According to this programme morphine is the drug of choice for patients with advanced disease having such severe pains that they need a strong opioid. It has thus been found that morphine is both efficacious and acceptable.

Opioids such as morphine must be administered in an acceptable form. The oral route is the best, because it spares the patient the discomfort of injections; it also maintains the patient's independence, since he or she does not have to rely on someone else for the next dose.

Morphine can be administered as a simple aqueous solution of morphine sulphate (or hydrochloride) in a range of strengths (e.g. 1 mg of morphine sulphate per ml to 20 mg per ml).

The effective analgesic dose of morphine varies considerably and ranges from as little as 5 mg to more than 200 mg. In many patients, pain is satisfactorily controlled with doses of between 5 and 30 mg every 4 hours. However, the dosage varies greatly for different patients because of wide individual variations in the oral bioavailability of the drug; the appropriate dose is the one that works. The drug must be given by the clock, i.e. at regular intervals, and not only when the patient complains of pain. The use of morphine is dictated by intensity of pain and not by brevity of prognosis.

Sustained-release morphine tablets are available in some countries in strengths varying from 10 to 200 mg. The most widely available strength is 30 mg. The dominating product is called a.o. MST Continus, MS Contin or MST. In vitro release data as well as pharmacokinetic data for this product, showing a major part of the active ingredient released and absorbed already within the first two or three hours, suggest that its properties are not adequate for a convenient dose schedule. While the manufacturer recommends up to 12-hours dosing intervals, extensive clinical experience suggests that an 8-hours interval is more realistic for continuous pain control.

In order to avoid pain periods due to inadequate compliance and to keep the patient constantly pain free, the administration of the analgesic drug must interfere as little as possible with the daily life. Twice daily administration is a reasonable solution but once daily administration is the ultimate goal. Another reason for developing preparations of long duration is that the patients in question are often very sick and need assistance for the medication. It would therefore be advantageous both for the patient and for the medical staff if a preparation for once a day administration would be available.

However, up to now it has not been considered feasible to make an oral morphine controlled release preparation which can be taken less than twice a day and still provide satisfactory bioavailablity, satisfactorily high plasma levels and pain relief. It has thus been considered that morphine can be sufficiently absorbed only during the comparatively short period when the morphine is in the stomach and small intestine from which follows that it would not be possible to make a morphine preparation which can be administered once per 24 hours and still give effective pain relief.

It has furthermore been considered impossible to make oral preparations with good controlled release properties from drug substances with high aqueous solubility, such as morphine sulphate. In the European Patent Application 0 377 518 it is suggested that sustained release preparations of highly soluble active substances such as morphine sulphate should be prepared with different release rates in the stomach and in the intestine, the active substance being available for absorption at a relatively faster rate in the intestine.

Other patent publications disclosing morphine preparations are the European Patent Publications 97 523 and 205 282, the U.S. Pat. Nos. 4,461,598 and 4,970,075 as well as the DD patent publications 295 548.

SUMMARY OF THE INVENTION

It has now unexpectedly been found that the controlled release preparation according to the present invention, which preparation is characterized by an essentially constant, zero order and pH independent release of the active compound, exhibits in vivo and in vitro data of morphine which are superior to those of the prior art.

Thus an object of the present invention is to provide an oral controlled release morphine preparation having a prolonged drug release as compared with the preparations presently available. The in vitro released amount after 8 to 12 hours should not reach 100%, and preferably be less than 90% in order to reach dosing intervals of 12 to 24 hours. Specifically the in vitro release after 12 hours should be more than 50, preferably more than 60% of the total amount of morphine. The release after 8 h should be less than 85, preferably less than 80, and more than 30, preferably more than 40%. It is understood that the release shall be of an essentially constant rate for the majority of the release period and neither, as is the case for existing products, a very rapid release for the first few hours and a considerably slower release thereafter, nor as is stated in the European Patent Application 0 377 518 a faster release in the intestine than in the stomach. This is to make it possible to have even plasma morphine levels and thus adequate pain control even with dose intervals of 12 to 24 hours.

A second object is to provide an oral controlled release morphine preparation having essentially complete bioavailability. In this context the term "complete bio-availability" means essentially the same bioavailability as a conventional, easily soluble oral morphine preparation.

Another object of the invention is to provide an oral controlled release morphine preparation for twice or preferably once a day administration.

According to one embodiment of the invention it has been found that a controlled release system, in which the release of morphine is controlled by diffusion, such as disclosed in the U.S. Pat. No. 4,557,925, to Lindahl et al. which is hereby incorporated by reference, can be used for the manufacture of a morphine preparation according to the invention. It has been found in this invention that a controlled release tablet manufactured according to this invention and with a morphine release over up to 24 hours has complete bioavailability. It has been found in this invention that a constant release almost independent of pH can be achieved with the membrane coating technique described above. By adding suitable amounts of pH regulating buffering substances to the composition, the pH inside the coating membrane can be kept at a level where the drug substance is easily dissolved and the release rate will be almost independent of pH.

BRIEF DESCRIPTION OF THE DRAWINGS

The drawing presents data showing the plasma concentration made possible by a representative tablet in accordance with the present invention and by a commercial controlled release tablet for comparative purposes. It is seen that the morphine release from the preparation in accordance with the present invention is substantially constant during the 24 hours following the administration of a single table as described hereafter. On the contrary the plasma level resulting from the administration of the commercial tablet decreased rapidly after an initial peak.

DESCRIPTION OF PREFERRED EMBODIMENTS

According to the invention the morphine present in the core should be in an easily water soluble form, such as morphine chloride, morphine sulphate or any other water soluble salt acceptable for pharmaceutical use. The amount of morphine in each preparation can vary within a broad range and is usually between 10 and 200 mg calculated as sulphate.

Buffering agents are necessary for the diffusion controlled release in the intestines and can be selected from buffering agents acceptable for oral pharmaceutical use e.g. sodium bicarbonate, citric acid or tartaric acid.

A slow-release tablet according to the present invention and prepared according to the U.S. Pat. No. 4,557,925 could thus comprise a morphine containing tablet and a coating surrounding the same. The coating should be insoluble in water and in the gastrointestinal fluids and essentially consist of a terpolymer of vinyl chloride, vinyl acetate and vinyl alcohol and a pore-creating substance being randomly distributed in the polymer. The pore-creating substance should be present in an amount of 1–20 parts for each 1–10 parts of terpolymer.

The method of producing the coated tablet comprises the steps of dissolving the terpolymer in a solvent, preparing a suspension of the pore-creating substance, providing a pharmaceutical tablet, combining the suspension or solution of pore-creating substance and solvent solution of the terpolymer to form a coating fluid, applying the coating fluid in the form of a solution or suspension to the tablet, and drying the coating fluid on the tablet to provide a terpolymer-coated tablet having the water-soluble pore-creating substance randomly distributed within the coating.

Preferably the terpolymer contains 80–95% weight per weight of vinyl chloride, 1 to 19% weight of vinyl acetate and 1 to 10% weight per weight of vinyl alcohol.

The pore-creating substance used according to the present invention should be highly water-soluble, pharmacologically acceptable. Especially preferred as pore-creating substance is saccarose (sucrose). Other substances which may be used include polyvinyl pyrrolidone, polyethylene-glycol 1500, 4000 or 6000 and sodium chloride.

The ratio pore-creating agent to terpolymer depends on the desired dissolution rate and time and can be decided in each separate case from simple experiments in the laboratory. Generally, it can be said that in order to get practically useful dissolution from tablets for oral use the ratio should vary between 1 and 5, preferable between 1.5 and 3.

The particle size of the pore-creating substance may vary between 0.5 and 50 millimicrons.

Preferably a plasticizer is also present in the terpolymer. The amount of this plasticizer may vary between 0.1 and 4% weight by weight of the coating fluid. Examples of suitable plasticizers are acetyltributylcitrate, polyethylene glycol, blown castor oil and glyceryl triacetate. Furthermore, the coating may include sodium bicarbonate as stabilizing agent.

Depending on the size and area of the tablet the coating weight may vary between 10 and 170 mg per tablet and the coating thickness may vary between 25 and 300 μm, preferably 50 and 200 μm.

The coating mixtures are produced in the following manner:

1) A terpolymer containing (w/w %) 80–95% (vinylchloride), 1–19% VAC (vinylacetate) and 1–10% VOH (vinylalcohol) is dissolved in a solvent, e.g. acetone, methylenechloride, methylethylketone, or mixtures of acetone and ethanol, acetone and methylene chloride, or the like.

2) A suspension or solution of the pore-creating substance is produced as follows:

The pore-creating particles are ground either by dry milling in a ball mill or by wet-milling in a glass bead milling device to a defined particle size, preferably between 0.5 μm and 50 μm. The particles are dispersed in solvents or mixtures of solvents, such as those previously mentioned, and mixed with the terpolymer solution.

The ratio between pore-creating substance and terpolymer in the coating fluid is as previously described for the ratio in the coating. The coating fluid may, as previously stated, include a plasticizer and sodium bicarbonate.

The coating fluid, in the form of a suspension, is then applied on drug-containing cores by conventional coating procedure. Examples of such coating procedures are pan coating, manual or spray-coating. Würster coating, and other fluid-bed coating procedures. Coloring matter can also be incorporated in the coating fluid, and insoluble coloring materials are preferred.

A second coating can be applied, and may contain one or more same or different drugs, for which a rapid release is desirable. This coating fluid is preferable a water-based sugar coating and, therefore, a seal coating between the latter and the terpolymer membrance coating is frequently necessary or desirable.

Although the morphine preparation has been discussed above in the form of a single tablet it is obvious that it could also be manufactured in other forms e.g. in the form of a multiple units formulation.

The invention is further illustrated by, but should not be limited to, the following examples.

EXAMPLE 1

Coating on tablets containing morphine sulphate 30 mg. Composition of the coating fluid:

| Constituents: | Amount mg/tablet |
|---|---|
| Morphine Sulphate | 30.0 |
| Lactose | 86 |
| Microcrystaline Cellulose (Avicel PH 101) | 15 |
| Succinic Acid | 5 |
| Povidone (Kollidon 30) | 12 |
| Magnesium Stearate | 1–3 |
| Ethanol (99.5%)* | (10–20) |

*Evaporates during the process

| Constituents in coating: | mg/tablet |
|---|---|
| Terpolymer (VC)M (VAC)N (VOH)O, wherein VC is vinylchloride, VAC is vinylacetate and VOH is vinylalcohol, and wherein M = 31, N = 1 and O = 2 | 11 |
| Micronized powdered saccharose (particle size 1–10 μm) | 29 |
| Acetyl tributyl citrate | 2 |
| Blown castor oil | 1 |
| Sodium bicarbonate | 1 |
| Acetone* | 264 |

*Evaporates during process

The coating process is performed in a coating pan and the coating fluid is sprayed onto the tablets with an airless spray-coating device, as disclosed in the U.S. Pat. No. 4,557,925.

The enclosed graph discloses that the plasma concentration dissolution (nmol/l) of morphine from a tablet according to the above exemple is essentially constant during 24 hours after one administration of the tablet according the invention (study on 12 patients) whereas in the commercial controlled release tablet (values for MS Contin from Cancer 63: 2348–2354, 1989, FIG. 5) the plasma level decreases rapidly after an initial peak. By increasing the amount of morphine in the tablet core the plasma concentration can be correspondingly increased. Tablets having higher or lower release rates can be obtained by varying the coating composition.

EXAMPLE 2

MORPHINE SULPHATE 10 MG controlled release tablets

| | Amount mg/tablet | |
|---|---|---|
| Constituents: | M** | S*** |
| Tablet Core: | | |
| Morphine Sulphate | 10,0 | 10,0 |
| Lactose | 110 | 3,4 |
| Microcrystalline Cellulose (Avicel PH 101) | 15 | 20 |
| Succinic Acid | 1,6 | 1,7 |
| Povidone (Kollidon 30) | 12 | 1,7 |
| Magnesium Stearate | 2 | 1 |
| Etahnol (99,5%)* | (8) | (?) |
| Lactose (spraydried) | | 67,3 |
| Coating | | |
| Sucrose powder | 17 | 21 |
| Coating Polymer (according to ex 1) | 9,2 | 11 |
| Acetyl Tributyl Citrate | 1,6 | 1,9 |
| Castor Oil, polymerized | 1,2 | 1,4 |
| Sodium Hydrogen Carbonate | 0,63 | 0,76 |
| Titanium Dioxide | 1,2 | — |
| Ethyl Vanillin | 0,007 | — |
| Acetone* | (153) | (187) |

*Evaporates during the process
**M = medium release rate
***S = slow release rate MORPHINE SULPHATE 60 MG controlled release tablets

| | Amount mg/tablet | |
|---|---|---|
| Constituents | M** | S*** |
| Tablet Core: | | |
| Morphine Sulphate | 60,0 | 60,0 |
| Lactose | 67 | 52 |
| Succinic Acid | 9,4 | 9,4 |
| Povidone (Kollidon 30) | 12 | 12 |
| Magnesium Stearate | 2 | 2 |
| Etahnol (99,5%)* | (5) | (?) |
| Microcrystalline Cellulose (Avicel PH 101) | 0 | 15 |
| Coating: | | |
| Sucrose powder | 17 | 27 |
| Coating Polymer (according to ex 1) | 5,4 | 8,6 |
| Acetyl Tributyl Citrat | 0,92 | 1,5 |
| Castor Oil, polymerized | 0,70 | 1,1 |
| Sodium Hydrogen Carbonate | 0,63 | 0,99 |
| Titanium Dioxide | 1,0 | — |
| Red Iron Oxide | 0,21 | — |
| Ethyl Vanillin | 0,007 | — |
| Acetone* | (158) | 250 |

*Evaporates during the process
**M = medium release rate
***S = slow release rate MORPHINE SULPHATE 100 MG controlled release tablets

| Constituents: | Amount mg/tablet |
|---|---|
| Tablet Core: | |
| Morphine Sulphate | 100 |
| Lactose | 87 |
| Succinic Acid | 17 |
| Povidone (Kollidon 30) | 19 |
| Magnesium Stearate | 2 |
| Etahnol (99,5%) | (9) |
| Coating: | |
| Sucrose powder | 20 |
| Coating Polymer (according to ex 1) | 6,4 |
| Acetyl Tributyl Citrate | 1,1 |
| Castor Oil, polymerized | 0,83 |
| Sodium Hydrogen Carbonate | 0,74 |
| Titanium Dioxide | 0,25 |
| Red Iron Oxide (E 172) | 1,5 |

-continued

| Constituents: | Amount mg/tablet |
|---|---|
| Ethyl Vanillin | 0,008 |
| Acetone* | (186) |

*Evaporates during the process

The following table discloses the release rates (dissolution rates) according to USP XX Apparatus 2 (Paddle) for tablet compositions according to the previous examples of the invention.

| Dis. rate | Morphine Sulphate Tablet | | | | | | |
|---|---|---|---|---|---|---|---|
| | 10 mg | | 30 mg | | 60 mg | | 100 mg |
| time | S* | M** | S* | M** | S* | M** | M** |
| 4 h | 28 | 40 | 25 | 41 | 31 | 42 | 40 |
| 8 h | 65 | 73 | 53 | 72 | 54 | 77 | 72 |
| 12 h | 88 | 91 | 73 | 93 | 73 | 100 | 95 |
| 16 h | 98 | 98 | 90 | 102 | 92 | 102 | 98 |

*S = slow release rate
**M = medium release rate

We claim:

1. Oral morphine preparation, characterized by essentially complete bioavailability and an, for the major part of the dissolution, essentially zero order and essentially pH independent in vitro release of morphine for a period of at least 8 hours during which period less than 100%, and more than 50% of the total amount of morphine is dissolved, whereby the morphine is present in the form of an easily soluble salt in combination with a buffering agent, whereby the preparation is coated with a diffusion membrane comprising a polymer which is essentially insoluble in water and gastrointestinal fluids, in which polymer a water soluble pore-creating agent is randomly dispersed, which preparation, in steady state, provides effective plasma levels for a period of at least 24 hours.

2. Preparation according to claim 1, characterized by an in vitro release of morphine after 8 hours in the range of 30–85%.

3. Preparation according to claim 1, characterized in an in vitro release of morphine after 12 hours in the range of 50–100%.

4. Preparation according to claim 1, characterized in that it is formulated as a tablet, wherein the morphine and the buffering agent are included in the tablet core.

5. Preparation according to claim 1, characterized in that the morphine salt is morphine sulphate or morphine chloride or any other water soluble salt acceptable for pharmaceutical use.

6. Preparation according to claim 1, characterized in that the buffering agent is succinic acid, tartaric acid, citric acid or any other organic acid acceptable for pharmaceutical use.

7. Preparation according to claim 1, characterized in that it is formulated as a multiple unit preparation.

8. Preparation according to claim 1 for administration with 24 hours intervals.

9. Preparation according to claim 2, characterized in an in vitro release of morphine after 12 hours in the range of 50–100%.

10. Preparation according to claim 2, characterized in that it is formulated as a tablet, wherein the morphine and the buffering agent are included in the tablet core.

11. Preparation according to claim 3, characterized in that it is formulated as a tablet, wherein the morphine and the buffering agent are included in the tablet core.

12. Preparation according to claim 9, characterized in that it is formulated as a tablet, wherein the morphine and the buffering agent are included in the tablet core.

13. Preparation according to claim 2, characterized in that the morphine salt is morphine sulphate or morphine chloride or any other water soluble salt acceptable for pharmaceutical use.

14. Preparation according to claim 3, characterized in that the morphine salt is morphine sulphate or morphine chloride or any other water soluble salt acceptable for pharmaceutical use.

15. Preparation according to claim 4, characterized in that the morphine salt is morphine sulphate or morphine chloride or any other water soluble salt acceptable for pharmaceutical use.

16. Preparation according to claim 2, characterized in that the buffering agent is succinic acid, tartaric acid, citric acid or any other organic acid acceptable for pharmaceutical use.

17. Preparation according to claim 3, characterized in that the buffering agent is succinic acid, tartaric acid, citric acid or any other organic acid acceptable for pharmaceutical use.

18. Preparation according to claim 4, characterized in that the buffering agent is succinic acid, tartaric acid, citric acid or any other organic acid acceptable for pharmaceutical use.

19. Preparation according to claim 5, characterized in that the buffering agent is succinic acid, tartaric acid, citric acid or any other organic acid acceptable for pharmaceutical use.

20. Preparation according to claim 5, characterized in that it is formulated as a multiple unit preparation.

21. Preparation according to claim 1 wherein said in vitro release of morphine for a period of at least 12 hours is less than 100% and more than 50%.

22. Preparation according to claim 1 wherein said in vitro release of morphine for a period of at least 12 hours is less than 100% and more than 60%.

23. Preparation according to claim 1 wherein said in vitro release of morphine after 8 hours is in the range of 40–80.

24. Preparation according to claim 1, wherein said in vitro release of morphine after 12 hours is in the range of 60–100%.

25. Preparation according to claim 1, wherein said in vitro release of morphine after 12 hours is in the range of 80–100%.

26. Preparation according to claim 2, wherein said in vitro release of morphine after 12 hours is in the range of 60–100%.

27. Preparation according to claim 2 wherein said in vitro release of morphine after 12 hours is in the range of 80–100%.

* * * * *